United States Patent [19]

Shair et al.

[11] 4,111,679

[45] Sep. 5, 1978

[54] POLYQUATERNARY COMPOUNDS FOR THE CONTROL OF MICROBIOLOGICAL GROWTH

[75] Inventors: Salem A. Shair, Lake Zurich, Ill.; Stewart N. Paul, Mississauga; James E. Cairns, Islington, both of Canada

[73] Assignee: Chemed Corporation, Cincinnati, Ohio

[21] Appl. No.: 825,272

[22] Filed: Aug. 17, 1977

[51] Int. Cl.$^2$ .............................................. A01N 9/20
[52] U.S. Cl. ........................................ 71/67; 424/329
[58] Field of Search ............................ 71/67; 424/329

[56] References Cited

U.S. PATENT DOCUMENTS

| | | | |
|---|---|---|---|
| 3,299,138 | 1/1967 | Sreum et al. | 71/67 X |
| 3,738,945 | 6/1973 | Panzer et al. | 71/67 |
| 3,771,989 | 11/1973 | Pera et al. | 424/329 X |
| 3,943,255 | 3/1976 | Newkirk | 71/67 X |
| 4,018,592 | 4/1977 | Buckman et al. | 71/67 |
| 4,054,542 | 12/1977 | Buckman et al. | 71/67 X |

*Primary Examiner*—Catherine L Mills
*Attorney, Agent, or Firm*—Charles L. Harness

[57] ABSTRACT

Control of microorganisms in industrial recirculating water systems using polyquaternary amines.

3 Claims, No Drawings

POLYQUATERNARY COMPOUNDS FOR THE CONTROL OF MICROBIOLOGICAL GROWTH

The method of the present invention for controlling microorganisms in industrial cooling water systems comprises adding to the system a microbiocidal amount of a polyquaternary amine of the formula

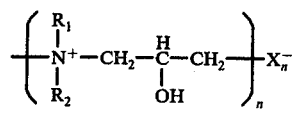

where $R_1$ and $R_2$ are methyl or ethyl, X is Cl, Br, or I, and $n$ is 3 to 10,000, preferably about 5–1,000. These polyquaternary amines are available commercially and can be made by reacting dimethyl (or diethyl) amine with epichlorohydrin, as described in U.S. Pat. No. 3,738,945. By "microbiocidal amount" we mean an amount which kills, inhibits the growth of, or prevents the growth of, microorganisms that tend to inhabit and proliferate in industrial cooling water systems. These microorganisms typically include (but are not limited to):

| Slime-forming Bacteria |
| --- |
| *Aerobacter aerogenes* |
| *Bacillus subtilis var. mycoides* |
| Algae |
| *Chlorella vulgaris* |
| *Oscillatoria sp.* |
| Other |
| *E. coli* |
| *P. aeruginosa* |

The aforesaid polyquaternary amines appear to be effective in controlling a broad range of bacteria, fungi, and algae, over a wide pH range, and at low dosages.

In the tests, description, and examples following, unless otherwise specified, the microbiocidal agent used was

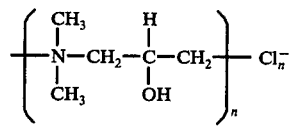

n = 500

The polyquaternary amines are known flocculants, and have been reported as flocculating river water and sewage. However, so far as we are aware, it was not previously known that these materials were effective in inhibiting the growth of microorganisms, whether or not in industrial cooling water systems.

This invention is of particular value in slime control in recirculating cooling water systems and in like systems.

Slime consists of certain biological organisms, many of them microscopic; accumulations caused by such organisms; and organic matter. The resulting deposits, called slime, are of varying characteristics, ranging from stringy, pasty, and gelatinous, to hard and horny.

The development of slime constitutes a major problem wherever it occurs, but particularly in industrial applications, such as air conditioning units, cooling water systems, etc. In cooling towers and air conditioning units, the growth of slime on portions thereof reduces severely the efficiency of the tower or unit to dispel heat. In such situations, the development of slime requires frequent removal, a costly and time-consuming operation. For these and other reasons, the prevention of the development of slime is of great importance.

The biological organisms most typically involved in the development of slime are algae, bacteria, and fungi. The most notorious slime-producing members of such groups are those which secrete a gelatinous material surrounding the cells as a capsule or sheath. Such organisms thereby produce materials which contribute significantly to the bulk of the resulting slime. Moreover, such secretion has the effect of embedding the organism, thereby making it more resistant to control.

While the particular organisms present in the development of slime vary greatly from location to location, and even at a given location, from time to time, representative slime-forming organisms include: Aspergillus spp.; Penicillium spp.; Candida spp.; Saccharomyces spp.; Aerobacter spp., Escherichia spp.; Alcaligenes spp.; and Bacillus spp. Yet other organisms involved in slime development include: Chlorella spp.; Spirogyra spp.; Oscillatoria spp.; Vaucheria spp.; Pseudomonas spp.; Salmonella spp.; Staphylococcus spp.; Pullularia spp.; and Rhizopus spp. It will be apparent that any reasonably good slime control agent must be effective against a broad spectrum of microorganisms. We consider the above polyquaternary amines to be especially efficacious in this regard.

EXAMPLE 1

Tests against bacteria, fungi (molds), and algae

Tests were run to
(a) determine the bacteriotoxic properties of the compound using the time lapse method; the test bacteria are representative of the "nuisance" organisms which are predominant in industrial cooling water systems;
(b) evaluate the fungitoxicity of the compound using a time lapse method; the fungi used in this evaluation are those commonly present in cooling water systems;
(c) screen the growth-inhibiting properties of the compound against several genera of algae. The inhibition test indicators included algae frequently found in cooling water systems. A time lapse study was used and the test compound was diluted to give the desired concentrations.

The results are given in Table I, below.

TABLE I

Relative Toxicity of Polyquaternary Amine Against a Mixed Bacterial Culture, Mold and Algae in a Time-Lapse Study of Dosage Versus pH

| Time (Hours) | Concentration (ppm) | | | | | | | |
| --- | --- | --- | --- | --- | --- | --- | --- | --- |
| | 10 | 25 | 50 | 100 | 150 | 200 | 250 | 300 |
| *Mixed Bacteria pH 7.0\** | | | | | | | | |
| 1 | 93.3 | 95.0 | 97.4 | 99.9 | 99.9 | 96.9 | 99.7 | 99.9 |
| 2 | 95.8 | 96.6 | 97.0 | 99.9 | 99.9 | 99.9 | 99.9 | 99.9 |
| 3 | 97.8 | 99.3 | 98.8 | 99.9 | 100.0 | 99.9 | 99.9 | 99.9 |
| 4 | 97.5 | 98.1 | 98.3 | 99.9 | 100.0 | 100.0 | 100.0 | 100.0 |
| 5 | 98.8 | 99.2 | 98.9 | 99.9 | 100.0 | 100.0 | 100.0 | 100.0 |
| 6 | 98.0 | 98.7 | 99.5 | 99.9 | 100.0 | 100.0 | 100.0 | 100.0 |
| *Mixed Bacteria pH 8.5\** | | | | | | | | |
| 1 | 96.0 | 93.6 | 96.6 | 90.0 | 95.4 | 95.6 | 98.6 | 99.5 |
| 2 | 98.0 | 96.1 | 98.3 | 99.8 | 99.9 | 99.9 | 99.9 | 99.9 |
| 3 | 95.6 | 98.8 | 99.2 | 99.9 | 99.9 | 99.9 | 99.9 | 99.9 |
| 4 | 96.0 | 97.8 | 98.3 | 99.9 | 99.9 | 100.0 | 100.0 | 100.0 |
| 5 | 97.8 | 98.1 | 98.5 | 100.0 | 99.9 | 100.0 | 100.0 | 100.0 |

TABLE I-continued

| 6 | 98.6 | 99.0 | 99.3 | 100.0 | 100.0 | 100.0 | 100.0 | 100.0 |
|---|------|------|------|-------|-------|-------|-------|-------|
| Mixed Mold pH 7.0* | | | | | | | | |
| 1 | 0 | 0 | 0 | 0 | 0 | | | |
| 2 | 0 | 37.5 | 0 | 66.25 | 37.5 | | | |
| 3 | 33.3 | 76.1 | 47.6 | 80.4 | 71.4 | | | |
| Mixed Mold pH 8.5* | | | | | | | | |
| 1 | 20 | 45 | 53.7 | 53.7 | 68.7 | | | |
| 2 | 13.3 | 0 | 60 | 80 | 46.6 | | | |

| | | | | | | |
|---|---|---|---|---|---|---|
| 1 | 4 | 0 | 0 | 0 | 0 | 0 |
| 2 | 4 | 0 | 0 | 0 | 0 | 0 |
| 3 | 4 | 0 | 0 | 0 | 0 | 0 |
| 4 | 4 | 0 | 0 | 0 | 0 | 0 |
| 5 | 4 | 0 | 0 | 0 | 0 | 0 |
| 6 | 4 | 0 | 0 | 0 | 0 | 0 |
| 3 weeks | 4 | 0 | 0 | 0 | 0 | 0 |
| Mixed Algae pH 8.5 | | | | | | |
| 1 | 4 | 0 | 0 | 0 | 0 | 0 |
| 2 | 4 | 0 | 0 | 0 | 0 | 0 |
| 3 | 4 | 0 | 0 | 0 | 0 | 0 |
| 4 | 4 | 0 | 0 | 0 | 0 | 0 |
| 5 | 4 | 0 | 0 | 0 | 0 | 0 |
| 6 | 4 | 0 | 0 | 0 | 0 | 0 |
| 3 weeks | 4 | 0 | 0 | 0 | 0 | 0 |

Interpretation of Algae Results

| Numerical Description | Estimated Percent Kill | Visual Description |
|---|---|---|
| 0 | 100% | No Growth |
| 1 | 75% | Scant Growth |
| 2 | 50% | Moderate Growth |
| 3 | 25% | Good Growth |
| 4 | 0% | Luxuriant Growth |

*Results expressed in % kill.

EXAMPLE 2

The following gives additional data relative to the activity of the polyquaternary amine against two pure cultures of bacteria (Table II) and two pure cultures of algae (Table III).

TABLE II

Percent Kill of Polyquaternary Amine Against *Aerobacter aerogenes* and *Bacillus subtilis var. mycoides* Versus Time pH 7.0 and 8.5

| | Aerobacter aerogenes* | | | | | | | | |
|---|---|---|---|---|---|---|---|---|---|
| Time | 5 | | 10 | | 25 | | 50 | | (ppm) |
| (hrs) | 7.0 | 8.5 | 7.0 | 8.5 | 7.0 | 8.5 | 7.0 | 8.5 | (pH) |
| 1 | 99.9 | 99.9 | 99.9 | 99.9 | 100 | 100 | 100 | 100 | |
| 2 | 100 | 100 | 100 | 100 | 100 | 100 | 100 | 100 | |
| 3 | 100 | 100 | 100 | 100 | 100 | 100 | 100 | 100 | |
| 4 | 100 | 100 | 100 | 100 | 100 | 100 | 100 | 100 | |
| 5 | 100 | 100 | 100 | 100 | 100 | 100 | 100 | 100 | |
| 6 | 100 | 100 | 100 | 100 | 100 | 100 | 100 | 100 | |
| *Bacillus subtilis ver. mycoides* | | | | | | | | | |
| Time | 5 | | 10 | | 25 | | 50 | | (ppm) |
| (hrs) | 7.0 | 8.5 | 7.0 | 8.5 | 7.0 | 8.5 | 7.0 | 8.5 | (pH) |
| 1 | 97.8 | 98 | 98.5 | 99.0 | 99.4 | 99.0 | 100 | 100 | |

TABLE II-continued

| 2 | 97.4 | 99 | 99.3 | 99.3 | 99.8 | 99.7 | 100 | 100 |
|---|---|---|---|---|---|---|---|---|
| 3 | 97.7 | 99 | 99.7 | 100 | 100 | 100 | 100 | 100 |
| 4 | 98.0 | 100 | 100 | 100 | 100 | 100 | 100 | 100 |
| 5 | 100 | 100 | 100 | 100 | 100 | 100 | 100 | 100 |
| 6 | 100 | 100 | 100 | 100 | 100 | 100 | 100 | 100 |

*Pure Cultures of Slime-forming Bacteria.

TABLE III

Percent Kill of Polyquaternary Amine Against Chlorella vulgaris and Oscillatoria sp. Versus Time pH 7.0 and 8.5

| | Chlorella vulgaris* | | | | | | | | | |
|---|---|---|---|---|---|---|---|---|---|---|
| Time | 50 | | 60 | | 80 | | 90 | | 100 | (ppm) |
| (Hours) | 7.0 | 8.5 | 7.0 | 8.5 | 7.0 | 8.5 | 7.0 | 8.5 | 7.0 | 8.5 | (pH) |
| 2 | 90 | 90 | 90 | 90 | 100 | 100 | 100 | 100 | 100 | 100 |
| 4 | 90 | 90 | 90 | 90 | 100 | 100 | 100 | 100 | 100 | 100 |
| 6 | 90 | 90 | 90 | 90 | 100 | 100 | 100 | 100 | 100 | 100 |
| 24 | 100 | 100 | 100 | 100 | 100 | 100 | 100 | 100 | 100 | 100 |
| 3 weeks | 100 | 100 | 100 | 100 | 100 | 100 | 100 | 100 | 100 | 100 |

| | Oscillatoria sp.** | | | | | | | | | |
|---|---|---|---|---|---|---|---|---|---|---|
| Time | 50 | | 60 | | 80 | | 90 | | 100 | (ppm) |
| (Hours) | 7.0 | 8.5 | 7.0 | 8.5 | 7.0 | 8.5 | 7.0 | 8.5 | 7.0 | 8.5 | (pH) |
| 2 | 50 | 50 | 60 | 60 | 75 | 75 | 100 | 100 | 100 | 100 |
| 4 | 60 | 60 | 75 | 75 | 75 | 75 | 100 | 100 | 100 | 100 |
| 6 | 75 | 75 | 100 | 100 | 100 | 100 | 100 | 100 | 100 | 100 |
| 24 | 80 | 80 | 100 | 100 | 100 | 100 | 100 | 100 | 100 | 100 |
| 3 weeks | 80 | 80 | 100 | 100 | 100 | 100 | 100 | 100 | 100 | 100 |

*Chlorella vulgaris - Green Algae
**Oscillatoria sp. - Blue Green Algae

As a preferred embodiment, we propose that the invention be used in industrial recirculating water systems, typically of the order of 35,000 gallons capacity, e.g., cooling towers or the like. We recommend for such use that the polyquaternary amine be added to the water on an average of 3 days per week, over a period of 4 weeks, in varying amounts sufficient to provide between about 50 and about 100 ppm of the total composition in the water, to prevent growth of microorganisms in the water. The aforesaid numerical recitals are preferred, not limiting.

When added to water of a cooling tower or the like, the microbiological control agents of this invention should usually be added to the sump of the tower at a point of maximum linear velocity of water. The dosage of the microbiocide and the frequency of feeding depends to some extent upon the type of growth and the severity of the infection. Typically, for a recirculating system an effective amount is about 1 to 500 ppm. In the case where once-through cooling water system is involved, the microbiocide can be injected directly to the heat exchanger. Once again the dosage and frequency of application depends on the type of growth. In a once through cooling water system, the dosage level is usually higher because of the lack of adequate retention time. For once-through systems an effective amount is typically about 2 to 1,000 ppm.

Conventional adjuvants may be admixed with the polyquaternary amines, e.g., surface-active dispersing and solubilizing agents, stabilizers, binders, inert finely divided solids, or solvents or other liquid carriers. Depending upon the particular manner in which the invention is to be practiced, such compositions can be employed directly as the treating composition to be added to the aqueous system or can be employed as concentrate compositions and further diluted to produce the treating composition.

What is claimed is:

1. The method for controlling microorganisms in industrial cooling water systems which comprises adding to the system a microbiocidal amount of a polyquaternary amine of the formula
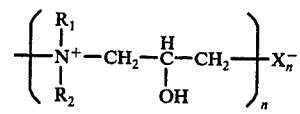
where $R_1$ and $R_2$ are methyl or ethyl, X is Cl, Br, or I, and $n$ is 3 to 10,000.
2. The method according to claim 1 in which $R_1$ and $R_2$ are methyl, X is Cl, and $n$ is about 500.
3. The method according to claim 2 in which the effective amount is 0.05 to 1000 ppm.
* * * * *